(12) United States Patent
Robinson et al.

(10) Patent No.: US 9,672,325 B2
(45) Date of Patent: Jun. 6, 2017

(54) METHODS AND APPARATUS FOR ESTABLISHING A HEALTHCARE DATA INTERFACE USING A PRACTICE MANAGEMENT SYSTEM

(71) Applicant: athenahealth, Inc., Watertown, MA (US)

(72) Inventors: Doran Robinson, Newton, MA (US); Justin Seger, Waltham, MA (US); Christopher Bassolino, Watertown, MA (US); James Sdoia, Wayland, MA (US); Bo Sun, Waltham, MA (US)

(73) Assignee: athenahealth, Inc., Watertown, MA (US)

( * ) Notice: Subject to any disclaimer, the term of this patent is extended or adjusted under 35 U.S.C. 154(b) by 292 days.

(21) Appl. No.: 14/090,048

(22) Filed: Nov. 26, 2013

(65) Prior Publication Data

US 2015/0149189 A1 May 28, 2015

(51) Int. Cl.
*G06Q 50/00* (2012.01)
*G06F 19/00* (2011.01)

(52) U.S. Cl.
CPC ................... *G06F 19/322* (2013.01)

(58) Field of Classification Search
CPC .......................... G06Q 50/22–50/24
See application file for complete search history.

(56) References Cited

U.S. PATENT DOCUMENTS

| | | |
|---|---|---|
| 4,858,121 A | 8/1989 | Barber et al. |
| 5,253,164 A | 10/1993 | Holloway et al. |
| 6,076,066 A | 6/2000 | Dirienzo et al. |
| 6,208,973 B1 | 3/2001 | Boyer et al. |
| 6,341,265 B1 | 1/2002 | Provost et al. |
| 6,343,271 B1 | 1/2002 | Peterson et al. |
| 7,016,856 B1 | 3/2006 | Wiggins |
| 7,447,988 B2 | 11/2008 | Ross |

(Continued)

OTHER PUBLICATIONS

U.S. Appl. No. 60/203,315, filed May, 10 2000, Ross.

(Continued)

*Primary Examiner* — Jonathan K Ng

(74) *Attorney, Agent, or Firm* — Wolf, Greenfield & Sacks, P.C.

(57) ABSTRACT

Methods and apparatus for establishing a healthcare data interface for a healthcare provider associated with a practice management system, wherein the healthcare data interface is established between the practice management system and a healthcare trading partner to enable electronic transmission of data between the practice management system and the healthcare trading partner. The method comprises receiving a request from the healthcare provider to establish the healthcare data interface with the healthcare trading partner and prompting, via a user interface, the healthcare provider for configuration information, wherein the prompting is performed based, at least in part, on information associated with the healthcare trading partner stored by the practice management system. The method further comprises receiving the configuration information from the healthcare provider, and configuring the healthcare data interface for the healthcare provider based, at least in part, on the received configuration information.

21 Claims, 9 Drawing Sheets

(56) References Cited

U.S. PATENT DOCUMENTS

| | | | |
|---|---|---|---|
| 2002/0032584 A1 | 3/2002 | Doctor et al. | |
| 2002/0082972 A1* | 6/2002 | Renwick | G06Q 30/06 705/37 |
| 2007/0027709 A1* | 2/2007 | Grate | G06Q 50/188 709/220 |
| 2008/0162496 A1* | 7/2008 | Postrel | G06Q 10/10 |
| 2008/0306926 A1* | 12/2008 | Friedlander | G06F 19/322 |
| 2010/0083171 A1* | 4/2010 | Begue | G06Q 30/06 715/810 |
| 2012/0023012 A1* | 1/2012 | Brousseau | G06F 17/30867 705/39 |
| 2013/0346109 A1* | 12/2013 | Gunn | G06Q 50/24 705/3 |
| 2014/0222712 A1* | 8/2014 | Samaha | G06Q 10/00 705/342 |

OTHER PUBLICATIONS

Civil Action No. 1:13-cv-10794-IT, athenahealth, Inc.'s Opening Claim Construction Brief, dated Jun. 27, 2014, filed Jun. 27, 2014. 23 pages.

Civil Action No. 1:13-cv-10794-IT, athenahealth, Inc.'s Proposed Claim Constructions and Support, dated Apr. 25, 2014, filed Apr. 25, 2014. 7 pages.

Civil Action No. 1:13-cv-10794-IT, athenahealth, Inc.'s Preliminary Identification of Claim Terms to be Construed, dated Apr. 11, 2014, filed Apr. 11, 2014. 3 pages.

Civil Action No. 1:13-cv-10794-IT, athenahealth, Inc.'s Replacement Claim Construction Reply Brief, dated Sep. 5, 2014, filed Sep. 10, 2014. 15 pages.

Civil Action No. 1:13-cv-10794-IT, CareCloud Corporation's Claim Construction Sur-Reply Brief, dated Oct. 6, 2014, filed Oct. 6, 2014. 16 pages.

Civil Action No. 1:13-cv-10794-IT, CareCloud Corporation's Identification of Claim Terms/Phrases for Construction, dated Apr. 11, 2014, filed Apr. 11, 2014. 4 pages.

Civil Action No. 1:13-cv-10794-IT, CareCloud Corporation's Preliminary Invalidity Contentions, dated Jan. 10, 2014, filed Jan. 10, 2014. 106 pages.

Civil Action No. 1:13-cv-10794-IT, CareCloud Corporation's Responsive Claim Construction Brief, dated Aug. 1, 2014, filed Aug. 1, 2014. 24 pages.

Civil Action No. 1:13-cv-10794-IT, Declaration of Chi Cheung in Support of CareCloud Corporation's Responsive Claim Construction Brief, .dated Aug. 1, 2014, filed Aug. 1, 2014. 40 pages.

Civil Action No. 1:11-cv-11260-GAO, "Advanced Billing Features," webpage found at http://web.archive.org/web/19981202203523/http://www.medicalmanager.com/v9/004.htm. 6 pages.

Civil Action No. 1:11-cv-11260-GAO, "Customization," webpage found at http://web.archive.org/web/19981205131953/http://www.medicalmanager.com/v9/007.htm . 3 pages.

Civil Action No. 1:11-cv-11260-GAO, "Electronic Communications," webpage found at http://web.archive.org/web/19981206025311/http://www.medicalmanager.com/v9/003.htm. 4 pages.

Civil Action No. 1:11-cv-11260-GAO, "Executive Summary," webpage found at http://web.archive.org/web/19990221040230/http://www.medicalmanager.com/v9/summary.htm. 6 pages.

Civil Action No. 1:11-cv-11260-GAO, "Introduction," webpage found at http://web.archive.org/web/19981205002805/http://www.medicalmanager.com/v9/intro.htm. 1 page.

Civil Action No. 1:11-cv-11260-GAO, "Patient Entry and Billing Cycles," webpage found at http://web.archive.org/web/19981206004426/http://www.medicalmanager.com/v9/002.htm. 6 pages.

Civil Action No. 1:11-cv-11260-GAO, Corrected Request for Ex Parte Reexamination of U.S. Pat. No. 6,343,271. Nov. 14, 2011. 1487 pages.

Civil Action No. 1:11-cv-11260-GAO, "Data Dictionary," webpage found at http://www.imaxsoft.com/docs/99%20Other%20Manuals/03%20IMAXSOFT%20Other%20Products/DOOR/DOOR%20V1_0/PDF/Facets%20Doc/FACETS/SA_REF.PDF; Facets Data Dictionary User Guide, Release 2.8. Dec. 1998. 73 pages.

Civil Action No. 1:11-cv-11260-GAO, Facets EDI 837 Outbound Claims Submission Subsystem User Guide, Release 2.8. Dec. 1998. 193 pages.

Civil Action No. 1:11-cv-11260-GAO, Facets Internet Applications Reference Guide, Release 2.8, Dec. 1998. webpage found at http://www.imaxsoft.com/docs/99%20Other%20Manuals/03%20IMAXSOFT%20Other%20Products/DOOR/DOOR%20V1_0/PDF/Facets%20Doc/FACETS/UPDATE.PDF. 74 pages.

Civil Action No. 1:11-cv-11260-GAO, Facets Product Overview, Fall 1997, webpage found at http://www.imaxsoft.com/docs/99%20Other%20Manuals/03%20IMAXSOFT%20Other%20Products/DOOR/DOOR%20V1_0/PDF/Facets%20Doc/FACETS/OVERVIEW.PDF. 42 pages.

Civil Action No. 1:11-cv-11260-GAO, Facets User Guide: System Administration Reference, webpage found at http://www.imaxsoft.com/docs/99%20Other%20Manuals/03%20IMAXSOFT%20Other%20Products/DOOR/DOOR%20V1_0/PDF/Facets%20Doc/FACETS/INTERNET.PDF. 134 pages.

Civil Action No. 1:11-cv-11260-GAO, Facets User Guide: System Administration Processing, webpage found at http://www.imaxsoft.com/docs/99%20Other%20Manuals/03%20IMAXSOFT%20Other%20Products/DOOR/DOOR%20V1_0/PDF/Facets%20Doc/FACETS/INTERNET.PDF. 306 pages.

Civil Action No. 1:11-cv-11260-GAO, Facets Product Update, Release 2.81, Mar. 1999, webpage found at http://www.imax.soft.com/docs/99%20Other%20Manuals/03%20IMAXSOFT%20Other%20Products/DOOR/DOOR%20V1_0/PDF/Facets%20Doc/FACETS/EDI837O.PDF. 394 pages.

Civil Action No. 1:11-cv-11260-GAO, Claimsnet.com Form 424B1, filed Apr. 8, 1999. 88 pages.

Civil Action No. 1:11-cv-11260-GAO, "Brochures," including all Brochure Index Links, http://web.archive.org/web/19980112180618/http://www.claimsnet.com/brochures/default.htm. 15 pages.

Civil Action No. 1:11-cv-11260-GAO, Medical Manager Corp. 1998 10-K, filed Mar. 23, 1999. 113 pages.

Civil Action No. 1:11-cv-11260-GAO, "Halley Exchange Demo Software," webpage found at http://web.archive.org/web/19971008140858/http://www.halley.com/intface.htm ("Halley Demo"). 5 pages.

Civil Action No. 1:11-cv-11260-GAO, "Halley Generated Reporting," (Complete Sample Reports), webpage found at http://web.archive.org/web/19971008140908/http://halley.com/hrept5.htm. 25 pages.

Civil Action No. 1:11-cv-11260-GAO, "Halley Exchange Demo Software," webpage found at http://web.archive.org/web/19971008140858/http://www.halley.com/intface.htm. (Native format). 1 page.

Civil Action No. 1:11-cv-11260-GAO, "Halley Reporting," webpage found at http://web.archive.org/web/19971008140908/http://www.halley.com/hrept5.htm. 2 pages.

Civil Action No. 1:11-cv-11260-GAO, "Halley Interface," webpage found at http://web.archive.org/web/19971008140858/http://www.halley.com/intface.htm. 4 pages.

Civil Action No. 1:11-cv-11260-GAO, "Halley Homepage," webpage found at http://web.archive.org/web/19971008140814/http://www.halley.com/ . 2 pages.

Civil Action No. 1:11-cv-11260-GAO, "Halley Overview," webpage found at http://web.archive.org/web/19971008140840/http://www.halley.com/overview.htm. 2 pages.

Civil Action No. 1:11-cv-11260-GAO, "Halley Exchanges," vol. 2, Winter 1996-1997, webpage found at http://web.archive.org/web/19971008141453/http://www.halley.com/nlett2.htm . 5 pages.

Civil Action No. 1:11-cv-11260-GAO, "Halley Reasons," webpage found at http://web.archive.org/web/19971008140848/http://www.halley.com/reason.htm . 2 pages.

(56) References Cited

OTHER PUBLICATIONS

Civil Action No. 1:11-cv-11260-GAO, Medicode, Inc.'s Amendment No. 2 to Form S-1, filed Nov. 18, 1997 ("Medicode 1997 S-1/A"). 133 pages.
Civil Action No. 1:11-cv-11260-GAO, "Medicode Overview," http://web.archive.org/web/19980626131906/http://www.medicode.com/html/aboutmedicode.html. 3 pages.
Civil Action No. 1:11-cv-11260-GAO, Webpage found at http://web.archive.org/web/19980626132238/http://www.medicode.com/index.html. 1 page.
Civil Action No. 1:11-cv-11260-GAO, "Claims Manager Overview," webpage found at http://web.archive.org/web/19980626132425/http://www.medicode.com/html/claimsmanager.html. 2 pages.
Civil Action No. 1:11-cv-11260-GAO, AFEHCT Presentation to HCFA, Jan. 14, 1997, webpage found at http://web.archive.org/web/19990202033335/http://www.afehct.org/information_library.html. 113 pages.
Civil Action No. 1:11-cv-11260-GAO, "Software Questions," webpage found at http://web.archive.org/web/19970411063248/http://www.claimsnet.com/html/claims_processor_questions.htm. 4 pages.
Civil Action No. 1:11-cv-11260-GAO, "Sample Claims," webpage found at http://web.archive.org/web/19970411063339/http://www.claimsnet.com/html/sample_claims.htm. 1 pages.
Civil Action No. 1:11-cv-11260-GAO, "Medical Services," webpage found at http://web.archive.org/web/19970411062445/http://www.claimsnet.com/html/medical_services.htm. 1 page.
Civil Action No. 1:11-cv-11260-GAO, "About Claimsnet," webpage found at http://web.archive.org/web/19970411062358/http://www.claimsnet.com/html/about_american_net_claims.htm. 1 page.
Civil Action No. 1:11-cv-11260-GAO, "Steps," webpage found at http://web.archive.org/web/19970411062637/http://www.claimsnet.com/html/7_easy_steps.htm. 1 page.
Civil Action No. 1:11-cv-11260-GAO, "Demo," webpage found at http://web.archive.org/web/19970411062653/http://www.claimsnet.com/html/claims_processor_demo.htm, including all linked steps of the demo. 6 pages.
Civil Action No. 1:11-cv-11260-GAO, "Erisco Overview," webpage found at http://web.archive.org/web/19971017134753/http://www.erisco.com/prdorvw.htm. 2 pages.
Civil Action No. 1:11-cv-11260-GAO, "Questions," webpage found at http://web.archive.org/web/19970411063301/http://www.claimsnet.com/html/claimsnet.com_questions.htm. 3 pages.
Civil Action No. 1:11-cv-11260-GAO, Health Data Directory. Bill Briggs ed. Faulkner & Gray 2000 ed. 1999. 212 pages.
Civil Action No. 1:11-cv-11260-GAO, "Electronic Claims," http://web.archive.org/web/20000303032008/http://www.accumedic.com/ele.htm . 1 page.
Civil Action No. 1:11-cv-11260-GAO, "HCIS Products," http://web.archive.org/web/20000301143435/http://www.hcis.com/products/index.htm. 3 pages.
Civil Action No. 1:11-cv-11260-GAO, Webpage found at http://web.archive.org/web/20000303084813/http://www.accumedic.com/index.htm. 1 page.
Civil Action No. 1:11-cv-11260-GAO, Webpage found at http://web.archive.org/web/20000517042344/http://www.hcis.com/index.htm. 1 page.
Civil Action No. 1:11-cv-11260-GAO, "VISION HomeCare Overview," Webpage found at ttp://web.archive.org/web/20000523231231/http://www.hcis.com/products/vision_descrip.htm. 2 pages.
Civil Action No. 1:11-cv-11260-GAO, PC-ACE Users Manual HCFA 1500, Release 4.30 Aug. 1996. 2 pages.
Civil Action No. 1:11-cv-11260-GAO, TX-ACE Users Manual HCFA 1500, Release 6.0 Jan. 1996. 284 pages.
Civil Action No. 1:11-cv-11260-GAO, Core Module Manual, Release 10.04. Jan. 2001. 1083 pages.
Civil Action No. 1:11-cv-11260-GAO, MedicWare Interface Manual, Release 10.03 Jul. 2001. 39 pages.
Civil Action No. 1:11-cv-11260-GAO, Technical Services Bulletin: Service Pack 2 SP2. May 7, 2001. 5 pages.
Civil Action No. 1:11-cv-11260-GAO, New Client Assistance Manual Oct. 2000. 99 pages.
Civil Action No. 1:11-cv-11260-GAO, ClickON Technology Brochure. 2 pages.

\* cited by examiner

Existing Global Interfaces

| Interface Vendor ID | Direction | Destination Vendor IDs | Incomplete | Configured | Errors | Notes |
|---|---|---|---|---|---|---|
| Total Vendors | | | 289 | 1742 | | |
| edit \| sync ABCLABS::ROUTE | IN | ABCLABS | 1 | 3 | | link 237394 - [3368] Shi Yin Wong MD - AMERICAN BIO CLINICAL LAB - Go Live |
| edit \| sync ACUPATH::ROUTE | IN | ACUPATH | 0 | 1 | | link Test Port: 11349; Production Port: 11350; Context Key: MSH6 |
| edit \| sync ADVANCEDMEDLAB::ROUTE | IN | ADVANCEDMEDLAB:LAB | 0 | 4 | | link 268755 - [4875] AML One Tunnel - Connectivity, Validation, Preview & Production |

ACUPATH:ROUTE athenaNet home patient calendar clinicals billing reports admin research athena help logout

1000

Add New Context

Add New Context

Effective Date

Notes: Test Port: 11349; Production Port: 11350; Context Key: MSH|6

Contact
Minning Xie
Interface Analyst

Destination Vendors: ACUPATH
Direction: IN add context

Vendor Configuration save notes

Configured Contexts

| | Context ID | Effective Date | Foreign ID | Overrides | Errors | Active Jobs |
|---|---|---|---|---|---|---|
| edit remove | 3202 | | 5522 | | | |

METHODS AND APPARATUS FOR ESTABLISHING A HEALTHCARE DATA INTERFACE USING A PRACTICE MANAGEMENT SYSTEM

BACKGROUND

Healthcare service providers often exchange healthcare data with other service providers. For example, patient samples collected at a medical practice may be sent to a laboratory for analysis, and the results of the analysis may be sent back to the medical practice to include in the patient's medical record. Many healthcare data transmissions between service providers in the healthcare system use paper-based methods, such as facsimile or providing paper documents to patients who bring the documents with them from one service provider to another.

With the recent adoption of electronic health records (EHRs) and other computer-based software in the healthcare community, many healthcare organizations are beginning to store data electronically rather than using paper-based documents. Despite the widespread adoption of electronic storage of health information, paper-based methods of healthcare data transmission are prevalent yet still among many healthcare providers due to the amount of work and cost typically associated with creating point-to-point computer-based interfaces between healthcare service provides to share data electronically.

SUMMARY

Some embodiments are directed to a method of establishing a healthcare data interface for a healthcare provider associated with a practice management system. The healthcare data interface is established between the practice management system and a healthcare trading partner to enable electronic transmission of data between the practice management system and the healthcare trading partner. The method comprises receiving a request from the healthcare provider to establish the healthcare data interface with the healthcare trading partner; receiving configuration information from the healthcare provider; and configuring the healthcare data interface for the healthcare provider based, at least in part, on the received configuration information.

Other embodiments are directed to a computer system providing a practice management system. The computer system comprises at least one communication interface configured to establish a healthcare data interface for a healthcare provider associated with the practice management system, wherein the healthcare data interface is established between the practice management system and a healthcare trading partner to enable electronic transmission of data between the practice management system and the healthcare trading partner. The computer system also comprises at least one processor programmed to: receive a request from the healthcare provider to establish the healthcare data interface with the healthcare trading partner; receive configuration information from the healthcare provider; and configure the healthcare data interface for the healthcare provider based, at least in part, on the received configuration information.

Other embodiments are directed to at least one computer-readable storage medium encoded with a plurality of instructions that, when executed by at least one computer, perform a method of establishing a healthcare data interface for a healthcare provider associated with a practice management system, wherein the healthcare data interface is established between the practice management system and a healthcare trading partner to enable electronic transmission of data between the practice management system and the healthcare trading partner. The method comprises receiving a request from the healthcare provider to establish the healthcare data interface with the healthcare trading partner; receiving configuration information from the healthcare provider; and configuring the healthcare data interface for the healthcare provider based, at least in part, on the received configuration information.

It should be appreciated that any combination of the foregoing concepts and additional concepts discussed in greater detail below (provided that such concepts are not mutually inconsistent) are contemplated as being part of the inventive subject matter disclosed herein.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 9 illustrates an administrative page of a user interface configured to display a plurality of global healthcare data interfaces associated with a practice management system in accordance with some embodiments; and FIG. 10 illustrates an administrative page of a user interface configured to enable a user to associate a healthcare provider or medical practice with a global healthcare data interface in accordance with some embodiments.

DETAILED DESCRIPTION

Figure 2:
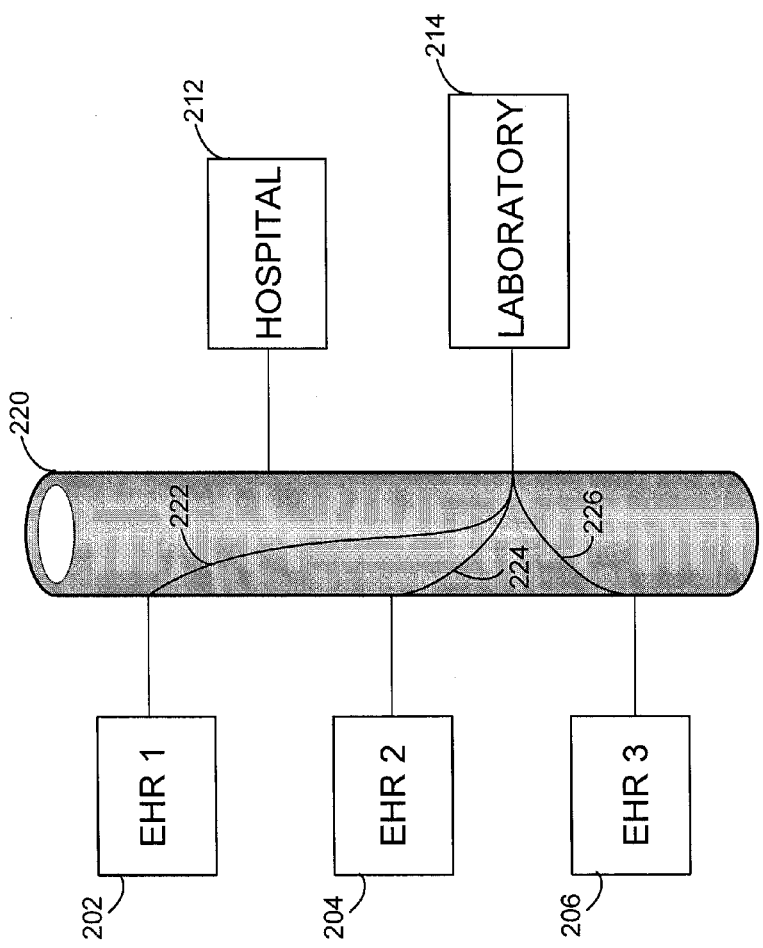
FIG. 2 is a schematic of a system for creating point-to-point healthcare data interfaces using a central hub that manages the interfaces.

The present disclosure generally relates to inventive methods and apparatus relating to establishing a healthcare data interface between a practice management system and a healthcare trading partner. Healthcare trading partners include, but are not limited to, entities that provide healthcare services, such as laboratories, pharmacies, and healthcare providers, and entities that provide one or more healthcare information technology services such as scheduling services, transcription services, collections services, and medical record exchange services. The healthcare data interface enables transmission of electronic data between the practice management system and the healthcare trading partner to provide healthcare providers associated with the practice management system a secure process for sending and receiving healthcare data respectively to and from healthcare facilities.

Some examples discussed below describe creating a healthcare data interface between a practice management system and a healthcare trading partner in response to a request from a healthcare provider associated with the practice management system. However, it should be appreciated that an instance of the healthcare data interface established between a practice management system and a healthcare trading partner may be configured for a single healthcare provider, a group of healthcare providers, a department at a healthcare facility (e.g., a medical practice), a healthcare facility, or a group of healthcare facilities, and not in response to such a request, and embodiments of the invention are not limited in this respect.

As discussed above, despite the increased usage of electronic health records (EHRs), healthcare providers often exchange health information with other service providers (also called "healthcare trading partners" herein) using paper-based methods such as facsimile or providing paper copies of physician orders or other healthcare materials to patients. For example, a laboratory may fax test results to a physician's office for review by a physician and/or inclusion in a patient's file, or staff at a hospital may fax a prescription to a pharmacy on behalf of a patient. When such information is received by the healthcare trading partner, staff at the trading partner are typically required to enter at least some of the information into an electronic system used by the trading partner to securely store health information. For example, health information received at a laboratory may be stored in a Laboratory Information Management System (LIMS) that enables the laboratory to manage workflow and data tracking at the laboratory. As a further example, received health information (e.g., laboratory test results) for patients of a medical practice may be manually entered into an EHR system by staff at the medical practice.

An alternative to transferring healthcare data using paper-based methods is to establish an electronic healthcare data interface between the healthcare entities to facilitate the exchange of electronic healthcare data using the healthcare data interface. In some systems, a healthcare data interface may be implemented as a direct point-to-point connection between the two healthcare entities. In such systems, each point-to-point connection is typically established and configured individually to ensure that the electronic data transferred between the two entities is in a format that can be interpreted by computer systems at each of the healthcare entities. For example, a first medical practice using a first type of EHR system and a second medical practice using a second type of EHR system may want to establish an electronic healthcare data interface to the same laboratory which uses a proprietary LIMS to manage laboratory data. To effectively communicate data between EHR systems at the medical practices and the LIMS at the laboratory, the healthcare data interface between each of the EHR systems and the LIMS must be configured to map data stored in the corresponding EHR system to data stored by the LIMS.

Often, an amount of time, resources, and cost associated with establishing and configuring a point-to-point connection that provides the mapping of data between healthcare entities are substantial, and may be cost-prohibitive for smaller medical practices with limited resources.

Figure 1:
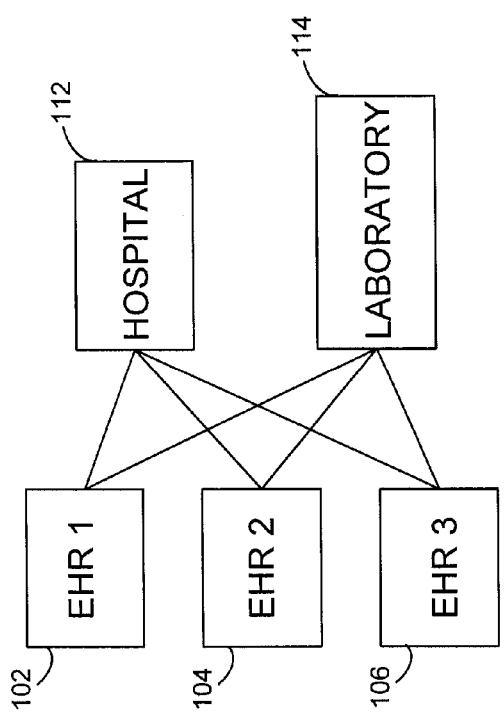
FIG. 1 is a schematic of a system for creating point-to-point healthcare data interfaces.

FIG. 1 illustrates a system for establishing direct point-to-point electronic healthcare data interfaces between a plurality of medical practices that use EHRs to store healthcare data and a plurality of healthcare trading partners. In the illustrative system of FIG. 1, medical practice 102 may use a first EHR system provided by a first vendor, medical practice 104 may use a second EHR system provided by a second vendor, and medical practice 106 may use a third EHR system provided by a third vendor. Each of the first, second and third EHR systems may store healthcare data differently (e.g., using different storage formats or schemes). Although in the illustrative system of FIG. 1, each of the medical practices uses a different EHR system, it should be appreciated that, in some embodiments, the same EHR system may be used by multiple medical practices, and the techniques described herein are not limited in this respect.

To establish a healthcare data interface with laboratory 114, a direct point-to-point connection is established between each of the EHR systems at the medical practices 102, 104, and 106 and the laboratory 114. Each healthcare data interface may be configured to ensure that electronic data sent from the corresponding EHR system to laboratory 114 is appropriately mapped to data fields in the data management system for the laboratory (e.g., the laboratory's LIMS). Additionally, each healthcare data interface may be further configured to ensure that electronic data (e.g., lab results) sent from laboratory 114 to each of the medical practices is mapped to the appropriate data fields in the medical practice's EHR system.

Medical practices may want to establish healthcare data interfaces with multiple trading partners to further reduce the use of paper-based methods for transferring health information. FIG. 1 also illustrates direct point-to-point connections for healthcare data interfaces between each of medical practices 102, 104, and 106 and hospital 112. For example, medical practice 102 may be a rural clinic that wants to transfer electronic health information to hospital 112 when a patient at the clinic is sent to the hospital to see a specialist rather than providing the patient with a paper form to take with him/her to the hospital. However, establishing a direct point-to-point connection to the hospital may be cost-prohibitive for the rural clinic due to the costs involved with establishing, configuring, testing, and maintaining the direct healthcare data interface. For example, hospital 112 may employ an EHR system different than that used by medical practice 102, and configuring the healthcare data interface may require mapping healthcare data fields between the two EHR systems to ensure that both systems can interpret the electronic healthcare data transferred via the healthcare data interface.

Establishing and configuring healthcare data interfaces between healthcare service providers often requires information technology personnel with specialized knowledge of healthcare information technology software. Some medical practices may not employ such personnel, but may contract with a third-party service provider who hosts a service to facilitate the establishment, configuration, and testing of healthcare data interfaces to transfer electronic healthcare data between healthcare entities.

FIG. 2 illustrates a system in which hub provider 220 provides services to establish, configure, and test healthcare data interfaces between medical practices 202, 204, and 206 and various healthcare trading partners including hospital 212 and laboratory 214. Hub 220 provides a common conduit for establishing point-to point connections between healthcare entities. Although hub 220 provides a centralized system for establishing point-to-point connections between each of the medical practices 202, 204, and 206 and healthcare trading partners, hospital 212 and laboratory 214, the process for establishing the healthcare data interfaces remains similar to that described above in reference to FIG. 1. For example, point-to-point connection 222 is established between medical practice 202 and laboratory 214, point-to-point connection 224 is established between medical practice 204 and laboratory 214, and point-to-point connection 226 is established between medical practice 206 and laboratory 214. Each of point-to-point connections 222, 224, and 226 is configured by hub 220 to map electronic healthcare data between the corresponding EHR/LIMS system to ensure that data transferred via the point-to-point connection may be interpreted by the receiving system. As discussed above, because each of medical practices 202, 204, and 206 may use an EHR system that is configured specifically for that medical practice and may store healthcare data differently, each of the point-to-point connections 222, 224, and 226 though while not direct connections (e.g., as shown in the system of FIG. 1), still require individual configuration by the service provider providing the hub 220 to ensure proper data transfer via each of the healthcare data interfaces.

Figure 3:
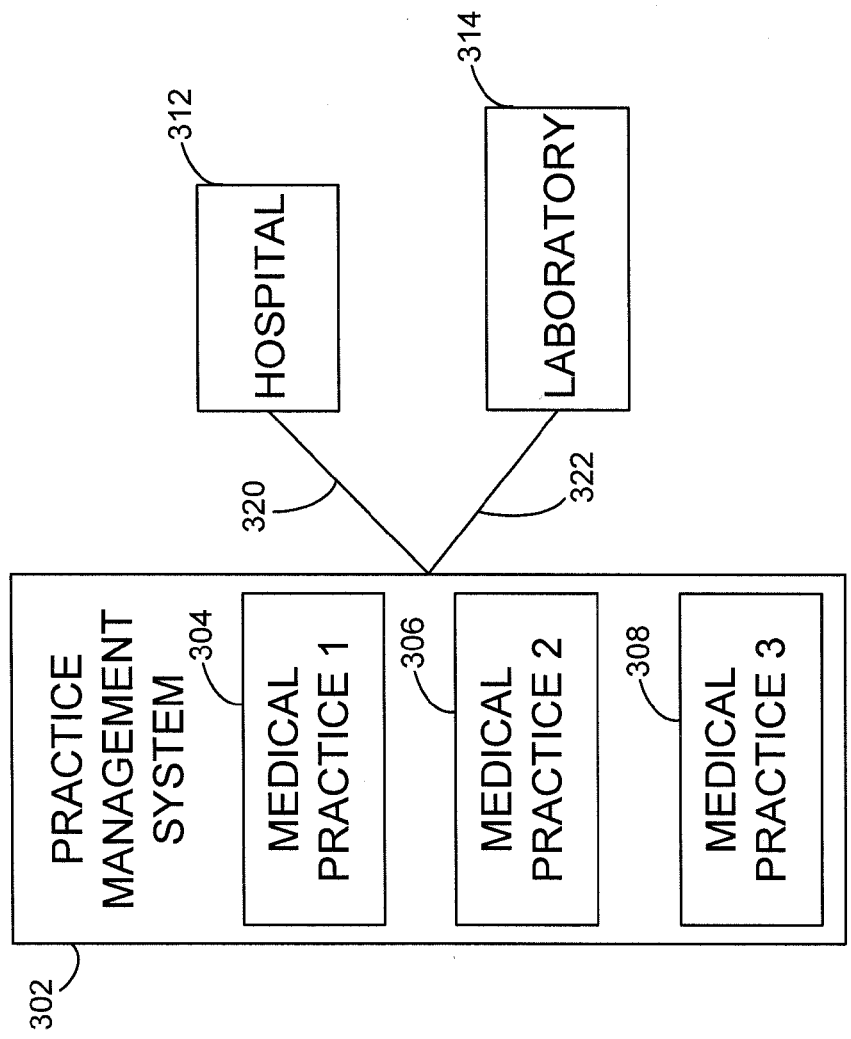
FIG. 3 is a schematic of a system for creating at least one global healthcare data interface between a practice management system and a healthcare trading partner in accordance with some embodiments.

The inventors have recognized and appreciated that establishing and configuring healthcare data interfaces may be improved for medical practices that are interested in having electronic data capabilities. FIG. 3 illustrates a schematic of a system in accordance with some embodiments. In the illustrative system of FIG. 3, each of medical practices 304, 306, and 308 is associated with a practice management system 302 to manage and store electronic health information for the medical practice. Because the same underlying EHR platform presented by the practice management system is used by each of medical practices 304, 306, and 308, each of the medical practices may utilize healthcare data interfaces 320 and 322 established between practice management system 302 and healthcare trading partners 312 and 314, as described in more detail below.

When establishing a healthcare data interface, a healthcare trading partner (e.g., hospital 312 or laboratory 314) may send to the practice management system, information required to configure the healthcare data interface for use by healthcare providers associated with practice management system 302. In response to receiving the configuration information (e.g., account number, provider ID), the practice management system may configure the healthcare data interface based, at least in part, on the received configuration information prior to enabling the healthcare provider to use the healthcare data interface to transfer electronic healthcare data to the healthcare trading partner.

Figure 4:
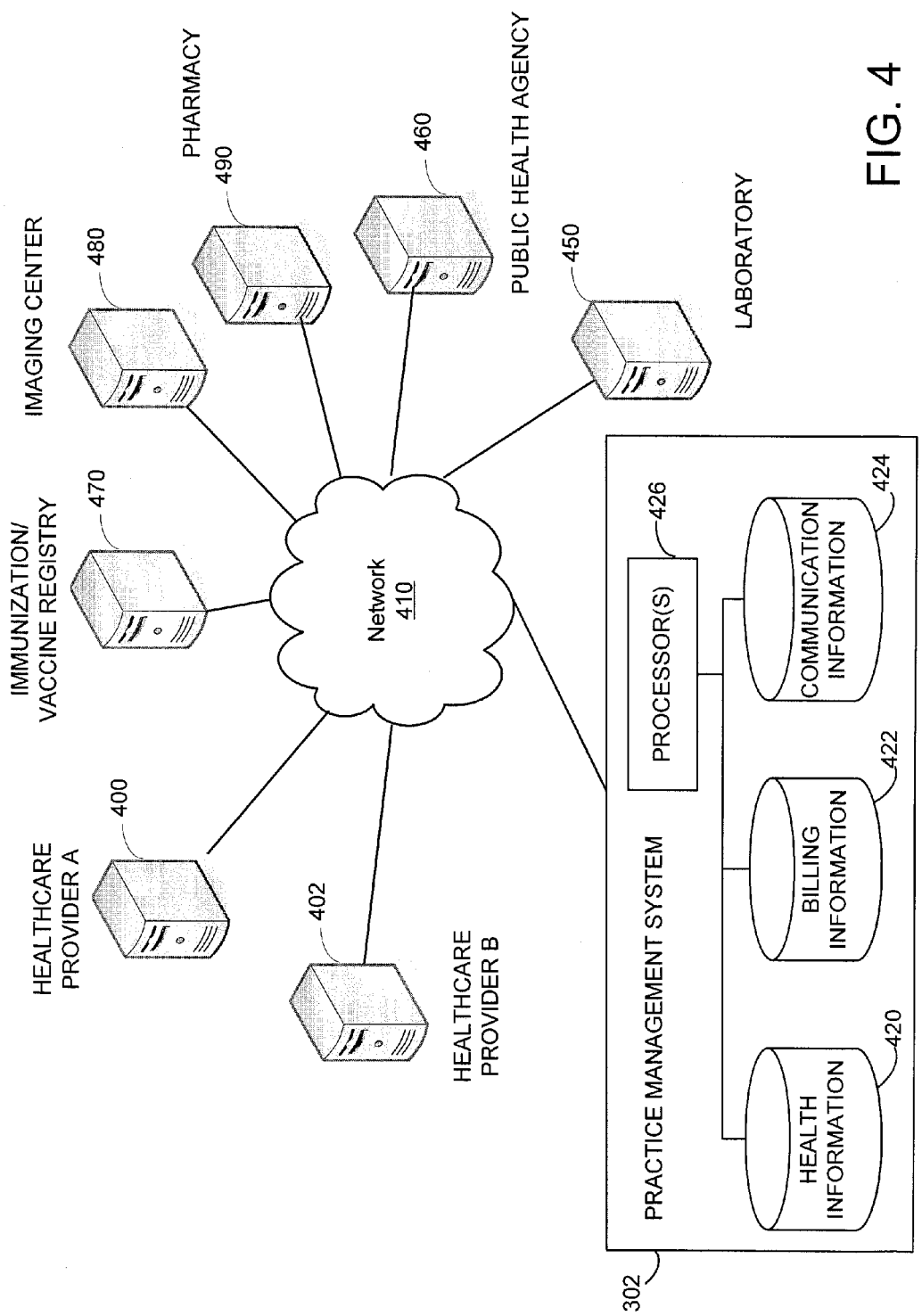
FIG. 4 is a schematic of an illustrative computer system on which some embodiments may be employed.

In some embodiments, a practice management system may establish a healthcare data interface with a healthcare trading partner using a direct connection. In other embodiments, a practice management system may establish a healthcare data interface with one or more healthcare trading partners via one or more public or private networks. FIG. 4 illustrates a networked system on which some embodiments may be employed. Networked computer 400 associated with a first healthcare provider, computer 402 associated with a second healthcare provider, and computer 302 located at a location associated with a practice management system, are shown connected to a network 410. Additionally, healthcare trading partners, examples of which include, but are not limited to, laboratory 450, public health agency 460, immunization/vaccine registry 470, imaging center 480, and pharmacy 490, are also shown connected to network 410. Network 410 may be any type of local or remote network including, for example, a local area network (LAN) or a wide area network (WAN) such as the Internet. Additionally, network 410 may include other entities than those shown in the FIG. 4.

In the example of FIG. 4, two networked computers for different healthcare providers and five healthcare trading partners are shown. However, it should be appreciated that network 410 may interconnect any number of computers of various types and the networked system of FIG. 4 is provided merely for illustrative purposes. For example, computer 302 may be connected via network 410 (or other networks) to a plurality of computers at a plurality of medical practice locations to provide practice management services to each of the connected medical practices. As should be appreciated from the foregoing, embodiments may be employed in a networked computer system regardless of the type or network size or configuration. Additionally, one or more of the computers in the networked system may be protected from unauthorized access using any suitable security protection devices or processes including, but not limited to, firewalls, data encryption, and password-protected storage.

In some embodiments, practice management system 302 may be a networked system that includes a plurality of components configured to perform tasks related to specific functions within the practice management system to facilitate the management of various aspects of medical practices including, billing, managing health information, and communications with patients.

Illustrative practice management system 302 includes health information management component 420, which is configured to store electronic health information for patients at medical practices including, but not limited to, electronic health records, lab results, imaging results, and orders prescribed by physicians at the medical practice. Health information management component 420 may include one or more processors programmed to manage the electronic health information stored thereon.

Practice management system 302 also includes billing management component 422, which is configured to facilitate the collection, submission, and tracking of claims filed by the medical practice to a plurality of payers (including patients) to ensure that the medical practice is properly compensated for medical services rendered to patients treated at the medical practice.

Practice management system 302 also includes communications management component 424, which interacts with health information management component 420 and billing management component 422 to facilitate interactions with patients on behalf of the medical practice using one or more communications channels including, but not limited to, a short messaging service (SMS) communication channel, a web-based communication channel, and phone-based communication channel, a wireless communication channel, and an e-mail based communication channel. In some embodiments, communications management component 424 may include a web-based portal implemented as a portion of a web application, with which patients may interact to perform a plurality of actions associated with services at a medical practice including, but not limited to, providing information about outstanding orders issued by a physician at the medical practice.

Although practice management system 302 is only shown as having three components, it should be appreciated that practice management systems for use with the techniques described herein may include any number of components (including less than three components) that interact in any suitable way. Furthermore, some or all of the components in practice management system 302 may interact by sharing data, triggering actions to be performed by other components, prevent actions from being performed by other components, storing data on behalf of other components, and/or interacting in any other suitable way.

Figure 5:
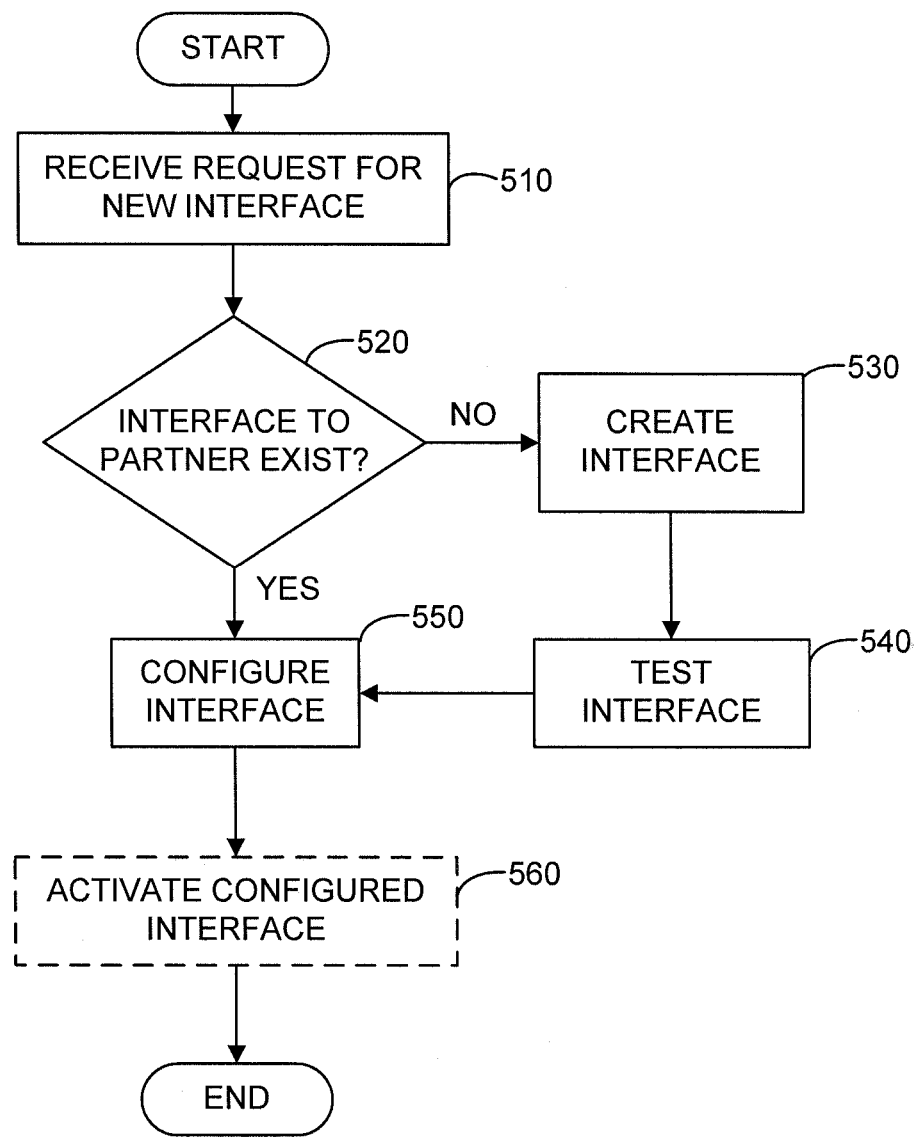
FIG. 5 is a flowchart of an illustrative process for establishing a healthcare data interface between a practice management system and a healthcare trading partner on behalf of a healthcare provider in accordance with some embodiments.

FIG. 5 illustrates a process for establishing a healthcare data interface in accordance with some embodiments. In act 510, a request to establish a new interface with a healthcare trading partner is received. The request to establish a new interface may be received in any suitable way. In some embodiments, a practice management system provides a user interface to enable a user (e.g., a healthcare provider, an administrator at a medical practice, or another authorized user of the practice management system) to specify a healthcare trading partner for a new healthcare data interface. For example, the practice management system may store information for one or more healthcare data interfaces that have been previously established between the practice management system and a healthcare trading partner, such as a laboratory, and the user interface may be configured to display identifying information for the healthcare trading partners for which a healthcare data interface has been previously established. For simplicity, healthcare data interfaces that have been previously established between the practice management system and a healthcare trading partner are referred to herein as "global healthcare data interfaces" or "global interfaces" to reflect that such interfaces may be used by one or more healthcare providers associated with the practice management system to transfer electronic data to the same healthcare trading partner, as discussed in more detail below.

In some embodiments, a request to establish a new interface may be received in response to a user interacting with the user interface provided by a practice management system. The user interface may enable a user to input an identifier for a healthcare trading partner with whom to establish the new interface. For example, in some embodiments, the user interface may display a search field that enables a user to input a complete or partial search information to identify the healthcare trading partner. If the entered search information does not match any healthcare trading partners for which a global interface has been established with the practice management system, the user may be prompted to provide additional information regarding the healthcare trading partner. In some embodiments, a drop-down menu or some other user interface element may be used to provide a list of healthcare trading partners for selection by the user for which a global interface has been established.

In some embodiments, one or more processors associated with a practice management system may be programmed to identify one or more healthcare providers associated with the practice management system that communicates healthcare data with at least one healthcare trading partner for which a healthcare data interface has already been established between the practice management system and the healthcare trading partner. For example, it may be determined that a healthcare provider associated with the practice management system sends on average twenty faxes per day to a laboratory for which a global healthcare data interface exists between the practice management system and the laboratory. By analyzing this behavior, the healthcare provider may be prompted to indicate that rather than faxing documents to the laboratory, an electronic healthcare data interface may be established for the healthcare provider using the existing global healthcare data interface. A request to establish the healthcare data interface may be received in response to prompting the user that a global healthcare data interface has already been created for the particular healthcare trading partner with which the healthcare provider frequently communicates using paper-based techniques.

Determining that a healthcare provider frequency communicates with a healthcare trading partner using primarily paper-based methods and that the healthcare provider could benefit from using an existing global healthcare data interface, may be performed in any suitable way using any suitable criteria. For example, in some embodiments, a single occurrence of a healthcare provider using a paper-based communication to a healthcare trading partner associated with a global interface may result in notifying the healthcare provider of the option to enroll with the global interface. Alternatively, detecting more than one occurrence and/or a frequency of occurrence of paper-based data transactions with a healthcare trading partner may be required prior to notifying the healthcare provider of the option to enroll with a global interface using the practice management system.

After receiving a request to establish a new interface, the process of FIG. 5 proceeds to act 520, where it is determined whether an interface for the healthcare trading partner identified in the request has been previously established (e.g., whether the practice management system has stored information associated with a global interface for the identified trading partner). Determining whether an interface exists for an identified healthcare trading partner may be accomplished in any suitable way. For example, when a user selects (e.g., via the user interface) a healthcare trading partner from a list of healthcare trading partners, the practice management system may automatically determine that a global interface has been established for the selected trading partner. In some embodiments, when a user interacts with the user interface to input an identifier for a healthcare trading partner (e.g., using a search interface), the practice management system may compare the identifier for the healthcare trading partner with information stored by the practice management system to determine whether the identified trading partner is associated with a global interface in the practice management system. Other techniques for determining whether an interface for an identified healthcare trading partner are also possible, and embodiments are not limited in this respect.

If it is determined in act 520 that an interface between the practice management system and the trading partner has not previously been established (e.g., the practice management system does not include information for associated with a global interface for the trading partner), the process proceeds to act 530 where a new global interface is created. Creation of a new global interface in accordance with some embodiments is described in more detail below. The process then proceeds to act 540, where the new global interface for the trading partner is tested to ensure that the new interface is configured appropriately to transfer healthcare data, as described in more detail below.

After the new global interface has been tested or when it is determined in act 520 that an interface previously existed for the requested trading partner, the process proceeds to act 550, where the healthcare data interface is configured for the user (e.g., healthcare provider) that provided the request in act 510 to establish the new healthcare data interface. A process of configuring a healthcare data interface for a user of a practice management system in accordance with some embodiments is also called "enrolling a user" with a healthcare data interface herein, and non-limiting examples of this process are discussed in more detail below.

After the healthcare data interface has been configured for the user, the process proceeds to act 560, where the configured interface is optionally activated to enable the healthcare provider to use the configured interface to transfer data to the healthcare trading partner indicated in the request. In some embodiments, after a healthcare data interface is configured in act 550 for a user of the practice management system (e.g., after a healthcare provider has been enrolled with the global interface), the configured interface may be immediately ready for use by the user with requiring activation act 560, as embodiments are not limited in this respect.

Figure 6:
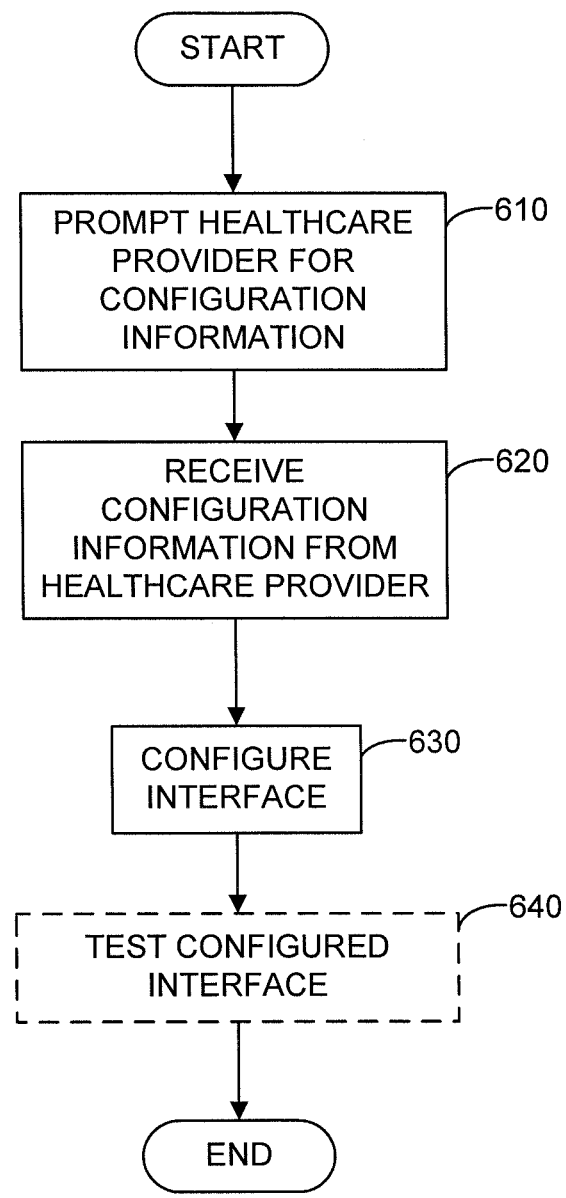
FIG. 6 is a flowchart of an illustrative process for enrolling a healthcare providers with a global healthcare data interface associated with a practice management system in accordance with some embodiments.

FIG. 6 illustrates a process for configuring a global healthcare data interface for use by a healthcare provider in accordance with some embodiments. After a global healthcare data interface has been selected for configuration, for example, as discussed above in connection with act 550 of the process of FIG. 5, the process of FIG. 6 begins in act 610, where a user (e.g., a healthcare provider) of a practice management system is prompted for configuration information to configure the selected healthcare data interface. The configuration information may be based, at least in part, on configuration requirements stored by the practice management system associated with the healthcare trading partner for the healthcare data interface.

As discussed in more detail below, in some embodiments, when a global data interface associated with the practice management system is created between a practice management system and a healthcare trading partner, the trading partner may send to the practice management system one or more configuration requirements for configuring the interface for a particular provider or medical practice. In some embodiments, at least some configuration requirements may also be specified by an administrator of a practice management system or from a third party source involved in facilitating the establishment of the healthcare data interface. Accordingly, it should be appreciated that configuration requirements may be received in any suitable manner from one or more entities, and embodiments are not limited in this respect. The received requirements for the global healthcare data interface may be stored by the practice management system in any suitable way, as embodiments are not limited in this respect.

In some embodiments, a user may be prompted for configuration information via a user interface, and the prompting may be performed based, at least in part, on stored configuration requirements associated with the healthcare trading partner for the healthcare data interface. For example, the user interface may display a plurality of fields that enable the user to enter the required configuration information for the healthcare data interface. Examples of configuration information includes, but is not limited to, a customer identification number and an account number. In some embodiments, each healthcare provider associated with a practice management system may be assigned a unique customer identification number that is used to associate data stored by the practice management system with the healthcare provider. Additionally, healthcare trading partners may assign unique account numbers to healthcare providers associated with the practice management system.

After the user has been prompted for the relevant configuration information, the process proceeds to act 620, where the configuration information is received (e.g., via the user interface) from the user. The process then proceeds to act 630, where the healthcare data interface is configured based, at least in part, on the received configuration information. In some embodiments, configuring a healthcare data interface comprises creating by the practice management system, a new instance of the global healthcare data interface, wherein the new instance is configured based, at least in part, on the received configuration information. For example, continuing with the example described above where the configuration information includes a provider identification number and an account number, this information may be used to configure an instance of a healthcare data interface between the provider corresponding to the provider identification number and a portion of the trading partner's computer system associated with the provider's account number. Other configuration information may also be prompted for, received, and used to configure a healthcare data interface in accordance with embodiments, and the techniques described herein for establishing healthcare data interfaces using a practice management system are not limited in this respect.

After configuring the healthcare data interface based on configuration information from a user, the process proceeds to act 640 where the configured data interface is optionally tested prior to activating the data interface for use. Any suitable testing may be performed to ensure that the data interface was configured properly, and embodiments are not limited in this respect. For example, one or more documents, images, or data may be transmitted between the practice management system and the healthcare trading partner to test the configured healthcare data interface.

As discussed above, a user (e.g., a healthcare provider) may request for a new data interface to be established for a healthcare trading partner that is not associated with a previously-configured data interface (e.g., the trading partner is not associated with a global healthcare data interface stored by the practice management system). In such instances, a new global interface may be created between the practice management system and the healthcare trading partner.

Figure 7:
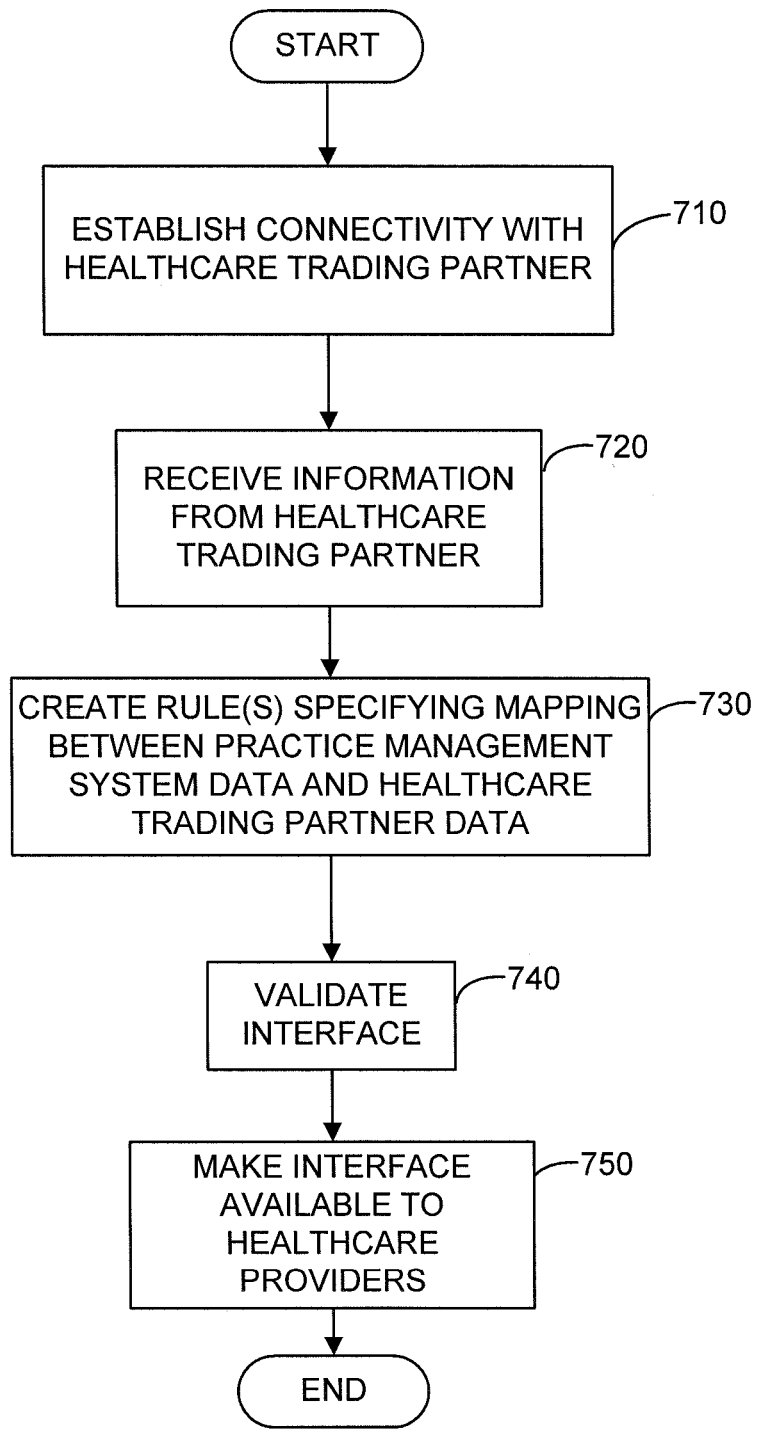
FIG. 7 is a flowchart of an illustrative process for creating a global healthcare data interface between a practice management system and a healthcare trading partner in accordance with some embodiments.

FIG. 7 illustrates a process for creating a new global healthcare data interface in accordance with some embodiments. After determining that a new global healthcare data interface is to be created, for example, as discussed above in connection with act 530 of the process of FIG. 5, the process of FIG. 7 begins. In act 710, connectivity is established between the practice management system and a computer system associated with the healthcare trading partner. Connectivity may be established in any suitable way, as embodiments are not limited in this respect. For example, in some embodiments, a virtual private network (VPN) may be established between one or more computers associated with the practice management system and one or more computers associated with the healthcare trading partner, and information used to create the global interface may be transmitted and received using the VPN.

In other embodiments, one or more applications may be transmitted to at least one computer associated with the healthcare trading partner, and the one or more applications, when executed by the at least one computer associated with the healthcare trading partner may provide information directly or indirectly to one or more computers associated with the practice management system to facilitate the creation of the new global interface. The application(s) may be transmitted to the healthcare trading partner computer(s) in any suitable way. For example, a computer associated with the practice management system may provide the application(s) directly to a trading partner computer using any suitable communications network or protocol. Alternatively, the application(s) may be stored at a network-accessible location from which the computer associated with the healthcare trading partner may download the application(s).

After establishing connectivity with the healthcare trading partner, the process of FIG. 7 proceeds to act 720, where information from the healthcare provider is received by the practice management system via the established connectivity. The received information may be used to establish a framework for the healthcare data interface, as discussed in more detail below. In embodiments where the connectivity between the computer(s) associated with the practice management system and the computer(s) associated with the healthcare trading partner is a VPN, the information received from the healthcare trading partner may be received via the VPN. In embodiments where the connectivity is provided, at least in part, by one or more applications transmitted to the computer(s) associated with the healthcare provider, the information may be received from the healthcare trading partner via a network-based server (e.g., a web server) that receives data from the application(s) executing on the computer(s) associated with the healthcare provider. Computer(s) associated with the practice management system may download the information from the network-based server without having to create a direct connection (e.g., a VPN) with the computer(s) associated with the healthcare trading partner. Any suitable techniques for transferring information between computer(s) associated with the practice management system and the healthcare trading partner may additionally or alternatively be used, as embodiments are not limited in this respect.

The information received from the healthcare trading partner may be received in any format and may include any suitable information that helps facilitate the creation of the global data interface by establishing a framework for the interface. For example, the received information may include configuration requirements for enrolling a healthcare provider with the global data interface, once created. Additionally, the information received from the healthcare trading partner may include information that facilitates creation of a mapping between data stored by the practice management system and data stored by a computer system associated with the healthcare trading partner, as discussed in more detail below. For example, two laboratories as healthcare trading partners may use a different code or codes to refer to the same laboratory test. Information provided from each laboratory during creation of a global data interface may be used to map a data field for the laboratory test stored by the practice management system to the proper code or codes in each of the laboratories electronic data systems.

After receiving at least some information from the healthcare trading partner, the process proceeds to act 730, where one or more rules are created specifying a mapping between data stored by the practice management system and corresponding data stored by the electronic data system of the healthcare trading partner. For example, after connectivity between the practice management system and the healthcare trading partner has been established, an HL7-formatted message may be received by the practice management system via the connectivity and one or more fields in the received message may be mapped to one or more data fields in the health information component of the practice management system. Any number or type of rules may be created to map data fields between the two systems, and embodiments are not limited in this respect. Additionally, all or a portion of the data mapping process may be automated by the practice management system, the healthcare trading partner's data management system, or both the practice management system and the trading partner's data management system, and embodiments are not limited based on the extent to which the data mapping process is automated.

In some embodiments, at least some of the rules used to map data between fields in a health information component of a practice management system and a data management system of a healthcare trading partner may be created by one or more computers at the healthcare trading partner. For example, computer(s) at the healthcare trading partner may install a connectivity client that provides a tool through which one or more messages from the practice management system describing one or more data fields in the health information component of the practice management system may be presented. Personnel (e.g., an information technology administrator) at the healthcare trading partner may interact with the tool to create one or more rules to specify a data mapping between data stored by the practice management system and data stored by computer(s) at the healthcare trading partner. The connectivity client may provide the one or more rules specifying a data mapping to a secure network-connected server (e.g., a web server), accessible by the practice management system to facilitate the creation of the new global healthcare data interface. The practice management system may interact with the network-connected server to retrieve information about the one or more rules for the new global healthcare data interface. After receiving the information about the one or more rules, the practice management system may use this information to create the new global healthcare data interface in accordance with the techniques described herein.

After creating one or more data mapping rules, the process proceeds to act 740, where the healthcare data interface is validated. Due to the sensitive nature of healthcare data, governmental regulations often require that computer code used to create a healthcare data interface be tested to ensure an appropriate level of security is applied to the transferred healthcare data. For example, the Clinical Laboratory Improvement Amendments (CLIA) permits laboratories to electronically exchange laboratory data with a system the includes an electronic health record provided the laboratory data is transferred in accordance with security standards that ensure patient privacy.

In point-to-point healthcare data interfaces, described above, prior to activating the healthcare data interface, the data interface is typically required to be validated to meet these requirements. In some embodiments, an amount of validation required for a healthcare data interface may be reduced compared to conventional point-to-point data interfaces. In particular, after a global healthcare data interface has been established between a practice management system and a healthcare trading partner in accordance with some embodiments, additional providers can be enrolled with the global interface without the need to perform additional testing and validation, thereby increasing the efficiency and reducing the cost associated with establishing a healthcare data interface between healthcare entities. That is, because the codebase associated with the global healthcare data interface does not change when a new provider is enrolled with the global interface, further testing of the interface to satisfy governmental (or other) regulations may not be required.

Validating a new global healthcare data interface established in accordance with some embodiments may be performed in any suitable way. For example, one or more sample messages may be transmitted from a practice management system to the healthcare trading partner, or vice versa, using the global data interface, and one or more users may evaluate whether the sample messages are transmitted and/or interpreted properly by the practice management system and/or the data management system of the healthcare trading partner. Additionally, one or more screenshots or other images may be sent between the practice management system and a computer associated with the healthcare trading partner to allow the healthcare trading partner and/or an administrator of the practice management system to confirm that the global interface is appropriately configured.

After the global healthcare data interface has been validated, the process proceeds to act 750, where the global interface is made available via the practice management system to healthcare providers or other users of the practice management system to enroll with the global interface. In some embodiments, the new global healthcare data interface may be developed in a testing environment of the practice management system prior to validation, and after validation, the global healthcare data interface may be transitioned to a production environment of the practice management system. After the global interface is made available in the production environment of the practice management system, individual providers, medical practices, or other authorized users of the practice management system, may enroll with the global interface, as discussed above, prior to enabling a particular user to transfer healthcare data to the trading partner using healthcare data interface.

Figure 8:
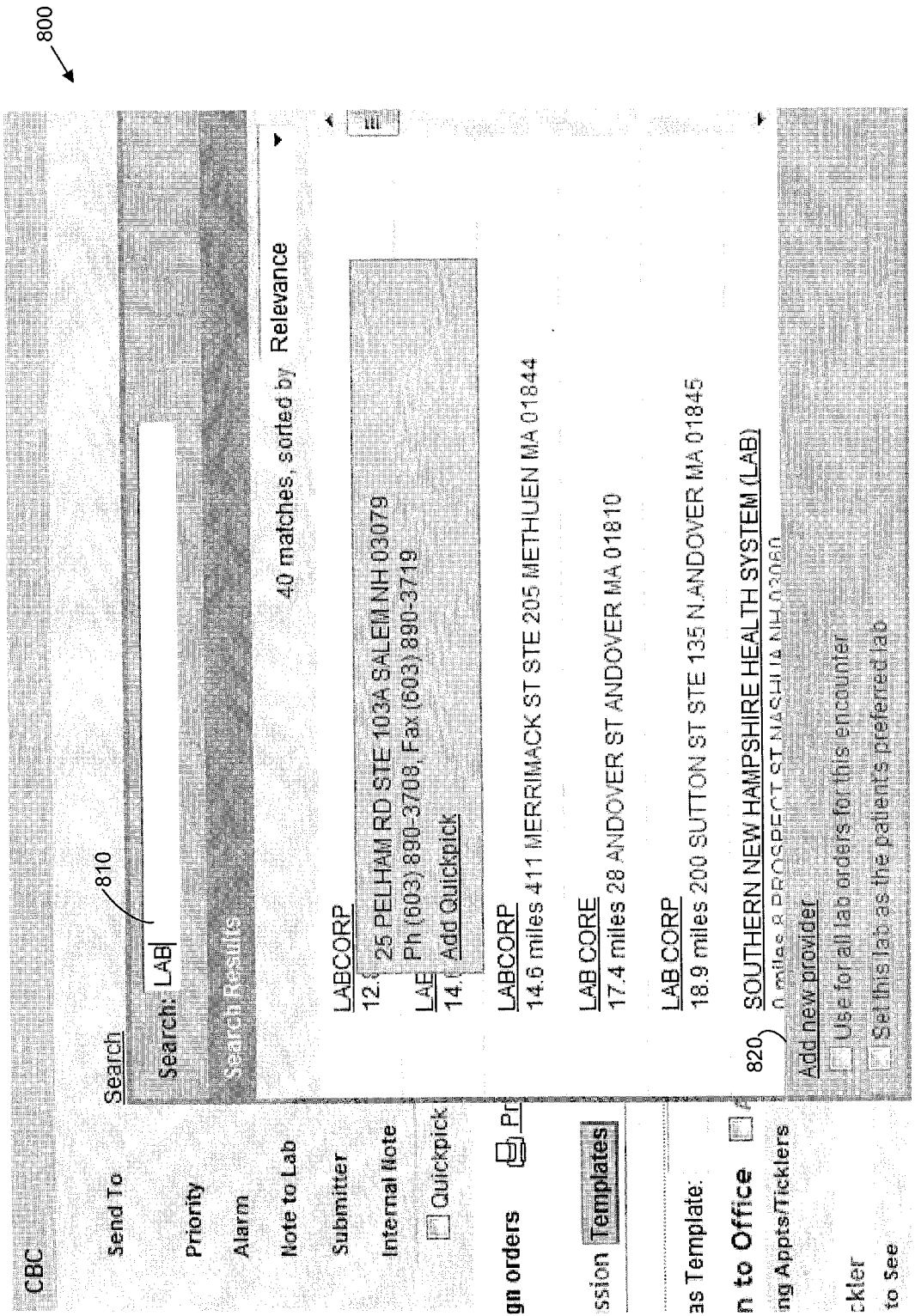
FIG. 8 illustrates a page of a user interface configured to enable a user to select a healthcare trading partner to enroll with a global healthcare data interface associated with a practice management system in accordance with some embodiments.

FIG. 8 illustrates a page 800 of a user interface that may be provided by a practice management system and displayed on computer of a healthcare provider, an administrator of a medical practice, or any other suitable user of the practice management system. The user interface of FIG. 8 displays a search interface to enable a user to search for a healthcare trading partner associated with the practice management system. The illustrative page 800 includes search field 810 with which a user may interact to specify a search string to identify the healthcare trading partner. In the example of FIG. 8, the user has specified "LAB" as the search string and in response, a plurality of laboratories associated with the practice management system are displayed on page 800. In some embodiments, the user may select one of the displayed laboratories to enroll in a global interface established between the practice management system and the laboratory. Alternatively, the user may interact with add new provider link 820 to enter information for a laboratory that is not associated with the practice management system. In response to specifying the new laboratory, the practice management system may initiate a process for creating a new global interface between the practice management system and the laboratory in accordance with the techniques described above.

The illustrative user interface 800 shown in FIG. 8 displays an interface for establishing (e.g., enrolling or creating) a healthcare data interface for a laboratory. However, it should be appreciated that a user interface for establishing a healthcare data interface for any suitable healthcare trading partner including, but not limited to, a pharmacy, a vaccine or immunization registry, a medical imaging facility, and a public health agency, may alternatively be used. In some embodiments, different user interfaces (or different portions of the same user interface) may be displayed to establish healthcare data interfaces for different types of healthcare trading partners, though embodiments are not limited based on how a user interface is configured to enable users of a practice management system to establish a healthcare data interface to a healthcare trading partner.

FIG. 9 illustrates a page 900 of a user interface that enables an administrator or other authorized user of a practice management system to associate a healthcare provider with a global interface that has been established between the practice management system and a healthcare trading partner. Page 900 displays a plurality of global healthcare data interfaces that have been created between a practice management system and a healthcare trading partner, such as a laboratory. The illustrative page 900 also shows the number of instances of each global healthcare data interface that have been configured for a particular healthcare provider and how many instances of the global interface have been initiated, but have not yet completed being configured prior to use by a healthcare provider. For example, three healthcare providers have been configured to use the global interface with the healthcare trading partner "ABCLABS," and one instance of this global interface has been created, but has not yet been fully configured for another healthcare provider. A user may interact with selector 910 to enroll a new healthcare provider with the corresponding global interface.

FIG. 10 illustrates a page 1000 of a user interface for enrolling a new healthcare provider with a global interface established between a practice management system and a healthcare trading partner. For example, in response to receiving a selection of a global interface on page 900, page 1000 may be displayed to enable an administrator or other authorized user of the practice management system to enter information about the healthcare provider to enroll with the selected global interface. The user may interact with one or more fields displayed on page 1000 to enter configuration information for the global interface to configure the interface for use by the healthcare provider. The fields displayed on page 1000 may be based, at least in part, on information provided by the healthcare trading partner associated with the global interface, as described above.

It should be appreciated that any authorized user of the practice management system may interact with pages 900 and 1000 to enroll a healthcare provider with a global interface, and an administrator of the practice management system is only one such type of user. For example, in some embodiments, a user (e.g., an administrator) at a medical practice associated with the practice management system may be provided access to enroll one or more healthcare providers at the medical practice with the global interface with little or no input from an administrator of the practice management system required. In such a self-service implementation, healthcare providers and medical practices may quickly enroll (or cease enrollment) with available healthcare trading partners as global interfaces between the practice management system and the healthcare trading partners become available. As should be appreciated from the foregoing, creating separate instances of a global interface using a practice management system provides a low-cost, efficient, and regulation-compliant technique for enabling healthcare providers to establish healthcare data connections with healthcare trading partners.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the techniques described herein comprises at least one non-transitory computer-readable storage medium (e.g., a computer memory, a USB drive, a flash memory, a compact disk, a tape, etc.) encoded with a computer program (i.e., a plurality of instructions) that, when executed on a processor, performs the above-discussed functions. The computer-readable storage medium can be transportable such that the program stored thereon can be loaded onto any computer resource to implement the aspects of embodiments discussed herein.

Various techniques described herein may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments in detail, various modifications and improvements will readily occur to those skilled in the art. Accordingly, the foregoing description is by way of example only, and is not intended as limiting.

What is claimed is:

1. A method of establishing an electronic healthcare data interface between a practice management system configured to store electronic health information for patients of a plurality of healthcare providers and a computer system of a healthcare trading partner to enable transmission of electronic healthcare data between the practice management system and the computer sustem of the healthcare trading partner, the method comprising:
   receiving a request from a first healthcare provider associated with the practice management system to establish the electronic healthcare data interface with the computer system of the healthcare trading partner;
   determining, by at least one processor of the practice management system, whether an electronic healthcare data interface was previously established between the practice management system and the computer system of the healthcare trading partner for a second healthcare provider associated with the practice management system;
   when it is determined that an electronic healthcare data interface was previously established between the practice management system and the computer system of the healthcare trading partner for the second healthcare provider:
      prompting, via a user interface presented by the practice management system, the first healthcare provider for configuration information, wherein the prompting is performed based, at least in part, on information associated with the healthcare trading partner stored by the practice management system;
      receiving the configuration information from the first healthcare provider; and
      configuring, by the at least one processor of the practice management system, the electronic healthcare data interface for the first healthcare provider based, at least in part, on the received configuration information and information about the previously established electronic healthcare data interface.

2. The method of claim 1, further comprising:
   determining whether the electronic healthcare data interface has been properly configured for the first healthcare provider; and
   activating the electronic healthcare data interface for the first healthcare provider after it has been determined that the electronic healthcare data interface has been properly configured.

3. The method of claim 1, wherein receiving the request from the first healthcare provider comprises receiving the request via the user interface presented by the practice management system.

4. The method of claim 3, further comprising:
   displaying on the user interface, identifiers for a plurality of healthcare trading partners associated with the practice management system for which at least one previous electronic healthcare data interface has been established using the practice management system, and wherein receiving the request via the user interface comprises receiving a selection of one of the identifiers for the plurality of healthcare trading partners displayed on the user interface.

5. The method of claim 1, further comprising:
   determining that the healthcare trading partner specified in the request is a new healthcare trading partner for which a previous electronic healthcare data interface has not been established with the practice management system; and
   establishing a framework for the electronic healthcare data interface based, at least in part, on information received from the new healthcare trading partner.

6. The method of claim 5, further comprising
   establishing connectivity between at least one first computer associated with the practice management system and at least one second computer of the computer system of the new healthcare trading partner; and
   receiving the information from the new healthcare trading partner via the connectivity established between the at least one first computer and the at least one second computer.

7. The method of claim 6, wherein establishing connectivity comprises establishing a virtual private network (VPN) connection between the at least one first computer and the at least one second computer.

8. The method of claim 6, wherein establishing connectivity comprises sending to the at least one second computer, an application that, when executed by the at least one second computer enables the at least one second computer to provide the information to the at least one first computer.

9. The method of claim 5, wherein establishing a framework for the electronic healthcare data interface comprises:
creating at least one rule specifying a mapping between data stored by the practice management system and data stored by the at least one second computer.

10. The method of claim 1, wherein the healthcare trading partner is selected from the group consisting of a laboratory, a pharmacy, a vaccine or immunization registry, a medical imaging facility, a healthcare facility, and a public health agency.

11. The method of claim 1, further comprising:
identifying at least one healthcare provider associated with the practice management system that communicates healthcare data with at least one healthcare trading partner for which an electronic healthcare data interface with the practice management system has been established;
determining whether the electronic healthcare data interface has been configured for use by the at least one healthcare provider; and
prompting the at least one healthcare provider when it is determined that the electronic healthcare data interface has not been configured for use by the at least one healthcare provider;
wherein the request is received in response to the prompt.

12. A computer-based practice management system configured to store electronic health information for patients of a plurality of healthcare providers, the computer-based practice management system comprising:
at least one communication interface configured to establish a healthcare data interface between the practice management system and a computer system of a healthcare trading partner to enable transmission of electronic healthcare data between the practice management system and the computer system of the healthcare trading partner; and
at least one processor programmed to:
receive a request from a first healthcare provider associated with the practice management system to establish the electronic healthcare data interface with the computer system of the healthcare trading partner;
determine whether an electronic healthcare data interface was previously established between the practice management system and the computer system of the healthcare trading partner for a second healthcare provider associated with the practice management system;
when it is determined that an electronic healthcare data interface was previously established between the practice management system and the computer system of the healthcare trading partner for the second healthcare provider:
prompt, via a user interface presented by the practice management system, the first healthcare provider for configuration information, wherein the prompting is performed based, at least in part, on information associated with the healthcare trading partner stored by the practice management system;
receive the configuration information from the healthcare provider; and
configure the electronic healthcare data interface for the first healthcare provider based, at least in part, on the received configuration information and information about the previously established electronic healthcare data interface.

13. The practice management system of claim 12, wherein the at least one processor is further programmed to:
display on the user interface, identifiers for a plurality of healthcare trading partners for which at least one previous electronic healthcare data interface has been established for a healthcare provider associated with the practice management system, and wherein receiving the request to establish the electronic healthcare data interface comprises receiving a selection of one of the identifiers for the plurality of healthcare trading partners via the user interface.

14. The practice management system of claim 12, wherein the at least one processor is further programmed to:
determine that the healthcare trading partner specified in the request is a new healthcare trading partner for which a previous electronic healthcare data interface has not been established with the practice management system; and
establish a framework for the electronic healthcare data interface based, at least in part, on information received from the new healthcare trading partner.

15. The practice management system of claim 14, wherein establishing a framework for the electronic healthcare data interface comprises creating at least one rule specifying a mapping between data stored by the practice management system and data stored by the computer system of the new healthcare trading partner.

16. The practice management system of claim 12, wherein the at least one processor is further programmed to:
identify at least one healthcare provider associated with the practice management system that communicates healthcare data with at least one healthcare trading partner for which an electronic healthcare data interface with the practice management system has been established;
determine whether the electronic healthcare data interface has been configured for use by the at least one healthcare provider; and
prompt the at least one healthcare provider when it is determined that the electronic healthcare data interface has not been configured for use by the at least one healthcare provider;
wherein the request is received in response to the prompt.

17. At least one non-transitory computer-readable storage medium encoded with a plurality of instructions that, when executed by at least one computer perform a method of establishing an electronic healthcare data interface between a practice management system and a computer system of a healthcare trading partner to enable transmission of electronic healthcare data between the practice management system and the computer system of the healthcare trading partner, the method comprising:
receiving a request from a first healthcare provider associated with the practice management system to establish the electronic healthcare data interface with the computer system of the healthcare trading partner;
determining, by at least one processor of the practice management system, whether an electronic healthcare data interface was previously established between the practice management system and the computer system of the healthcare trading partner for a second healthcare provider associated with the practice management system;

when it is determined that an electronic healthcare data interface was previously established between the practice management system and the computer system of the healthcare trading partner for the second healthcare provider:

prompting, via a user interface presented by the practice management system, the first healthcare provider for configuration information, wherein the prompting is performed based, at least in part, on information associated with the healthcare trading partner stored by the practice management system;

receiving the configuration information from the first healthcare provider; and configuring, by the at least one processor of the practice management system, the electronic healthcare data interface for the first healthcare provider based, at least in part, on the received configuration information and information about the previously established electronic healthcare data interface.

18. The computer-readable storage medium of claim 17, wherein the method further comprises:

displaying on the user interface, identifiers for a plurality of healthcare trading partners associated with the practice management system for which at least one previous electronic healthcare data interface has been established using the practice management system, and wherein receiving the request via the user interface comprises receiving a selection of one of the identifiers for the plurality of healthcare trading partners displayed on the user interface.

19. The computer-readable storage medium of claim 17, wherein the method further comprises:

determining that the healthcare trading partner specified in the request is a new healthcare trading partner for which a previous electronic healthcare data interface has not been established with the practice management system; and establishing a framework for the electronic healthcare data interface based, at least in part, on information received from the new healthcare trading partner.

20. The computer-readable storage medium of claim 19, wherein establishing a framework for the healthcare data interface comprises creating at least one rule specifying a mapping between data stored by the practice management system and data stored by the computer system of the new healthcare trading partner.

21. The computer-readable storage medium of claim 17, wherein the method further comprises:

identifying at least one healthcare provider associated with the practice management system that communicates healthcare data with at least one healthcare trading partner for which an electronic healthcare data interface with the practice management system has been established;

determining whether the electronic healthcare data interface has been configured for use by the at least one healthcare provider; and prompting the at least one healthcare provider when it is determined that the electronic healthcare data interface has not been configured for use by the at least one healthcare provider;

wherein the request is received in response to the prompt.

* * * * *

UNITED STATES PATENT AND TRADEMARK OFFICE
CERTIFICATE OF CORRECTION

| | | |
|---|---|---|
| PATENT NO. | : 9,672,325 B2 | |
| APPLICATION NO. | : 14/090048 | |
| DATED | : June 6, 2017 | |
| INVENTOR(S) | : Doran Robinson et al. | |

It is certified that error appears in the above-identified patent and that said Letters Patent is hereby corrected as shown below:

In Claim 1, at Column 15, Line 60, "computer sustem...." should read ---- computer system... ----.

In Claim 12, at Column 17, Lines 38-39, "establish a healthcare...." should read ---- establish an electronic healthcare.... ----.

In Claim 12, at Column 18, Lines 1-2, "from the healthcare...." should read ---- from the first healthcare.... ----.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*